United States Patent [19]

Debois

[11] Patent Number: 4,748,277

[45] Date of Patent: May 31, 1988

[54] PROCESS FOR THE PREPARATION OF TRIFLUOROMETHYLANILINES

[75] Inventor: Michel Debois, Rillieux, France

[73] Assignee: Rhone-Poulenc Specialites Chimiques, Courbevoie, France

[21] Appl. No.: 912,206

[22] Filed: Sep. 25, 1986

Related U.S. Application Data

[63] Continuation of Ser. No. 692,723, Jan. 18, 1985, abandoned.

[30] Foreign Application Priority Data

Jan. 20, 1984 [FR] France ................................ 84 00848

[51] Int. Cl.$^4$ .............................................. C07C 85/20
[52] U.S. Cl. .................................... 564/414; 564/394; 564/412

[58] Field of Search ....................... 564/394, 412, 414; 570/145

[56] References Cited

U.S. PATENT DOCUMENTS 4,466,927  8/1984  Lin et al. ........................ 260/544 C
4,481,370  11/1984  Lin et al. ............................ 564/394

Primary Examiner—Glennon H. Hollrah
Assistant Examiner—John A. Sopp
Attorney, Agent, or Firm—Finnegan, Henderson, Farabow, Garrett and Dunner

[57] ABSTRACT

A process for the preparation of trifluoromethylanilines. Hydrolysis and exchange fluorination of a para-trihalomethyl benzene isocyanate or carbamyl halide are carried out in liquid hydrofluoric acid.

14 Claims, No Drawings

PROCESS FOR THE PREPARATION OF TRIFLUOROMETHYLANILINES

This application is a continuation of application Ser. No. 692,723, filed Jan. 18, 1985, now abandoned.

The present invention relates to a process for the preparation of trifluoromethylanilines and more especially to a process for the preparation of para-trifluoromethylanilines.

It is known that para-trifluoromethylanilines may be prepared from p-chlorotrifluoromethylbenzene by ammonolysis, using the process of SEIWELL (J. Org. Chem. 1979, 44 (25), 4731-3) in an organic solvent, in the presence of cuprous chloride and potassium fluoride. The degree of conversion and the yield of p-trifluoromethylaniline are low and hence this process is difficult to exploit industrially.

Numerous processes have also been disclosed (J. Org. Chem. 26 (1961), 1477-80, J. Amer. Chem. Soc. 69 (1947), 2346-50) which use p-nitro-fluoromethylbenzene as a starting material, a catalytic reduction being carried out thereon. However, p-nitrotrifluoromethylbenzene is very difficult to obtain and hence this method cannot be used industrially.

There has also been disclosed, in French Pat. No. 1,545,142, a process for the preparation of trifluoromethylaniline from trifluoromethylisocyanates by hydrolysis in a sulfuric acid ($H_2SO_4$) medium. To obtain trifluoromethylphenylisocyanate, it is necessary to fluorinate trichloromethylphenylisocyanate in a hydrofluoric acid (HF) medium, followed by a difficult extraction from the HF medium to transfer the trifluoromethylphenylisocyanate into the $H_2SO_4$ medium where the hydrolysis takes place.

U.S. Pat. No. 4,466,927 discloses that 2-(trifluoromethyl)phenyl carbamic fluoride can be prepared by isomerizing N-(trifluoromethyl)-anthraniloyl fluoride in the presence of hydrogen fluoride. It is stated at column 3, beginning at line 9, that it is preferred to carry out the isomerization in the liquid phase to obtain the carbamic fluoride.

We have now found that it is possible to carry out the preparation of para-trifluoromethylanilines in a single stage, and with excellent yields, from paratrihalomethyl benzene isocyanates or carbamyl halides.

In effect, the present invention relates to a process for the preparation of para-trifluoromethylanilines which comprises simultaneously performing the hydrolysis and exchange fluorination of either a benzene isocyanate or a carbamyl halide, both of which carry a trihalomethyl group in the para-position, in liquid hydrofluoric acid.

For the purposes of the present invention, exchange fluorination refers to exchanging the halogens of the trihalomethyl group for fluorine atoms.

The benzene isocyanate or carbamyl halide has the general formula (I):

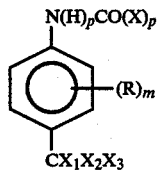

in which p is 0 or 1, X is a halogen, $X_1$, $X_2$ and $X_3$ are identical or different and each is a halogen atom, at least one of $X_1$, $X_2$ and $X_3$ is not fluorine, R is a group which is inert under the reaction conditions and is preferably chosen from among hydrogen, halogen, alkyl having from 1 to 4 carbon atoms, alkoxy, preferably $C_{1-4}$ alkoxy, alkylthio, preferably $C_{1-4}$ alkylthio, hydroxyl, carboxyl, nitro, carbonyl and cyano, and m is 1 or 2.

If p is 0, formula (I) represents an isocyanate and if p is 1, formula (I) represents a carbamyl halide.

The process is very especially suitable for compounds of the formula (I) where R is hydrogen and p is 0, as for example para-trichloromethylphenyl isocyanate, because the para-trifluoromethylaniline obtained in that case is a synthesis intermediate very widely used in the pharmaceutical and plant protection industries.

Carrying out the hydrolysis in a hydrofluoric acid medium greatly reduces the formation of urea.

The hydrofluoric acid used can be recycled, which is not possible if sulfuric acid is used, as in French Pat. No. 1,545,142. Moreover, use of hydrofluoric acid avoids having to change the reactor for the two stages of the process and does away with the technical problems caused by defluorination in a sulfuric acid medium.

To permit hydrolysis under optimum conditions, the hydrofluoric acid used preferably contains an amount of water such that the molar ratio of water to compound (I) is between about 1 and 2.

It is, however, more preferable still to use an amount of water such that the molar ratio of water to the compound of the formula (I) is about 1.

Since hydrofluoric acid is used as the reaction medium, the minimum amount must be such to allow the isocyanate to dissolve while the maximum amount is not critical and is simply chosen with a view to the economics of the process. It is, however, economically and industrially preferable to use a molar ratio of hydrofluoric acid to compound of the formula (I) which is between about 5 to 50.

The reaction is carried out at a temperature which is preferably between about 20° and 80° C.

If the hydrolysis is carried out at a temperature above 20° C., the reaction must be performed under pressure because the hydrofluoric acid must be liquid.

The reaction time varies from several minutes to several hours, and depends on the starting materials and on the reaction temperature.

The aniline obtained may be isolated in a manner well-known to those of ordinary skill in the art. For example, the hydrofluoric acid may be removed by distillation and can thus be recovered and recycled, this being an important advantage of the process of the invention. Thereafter the salt obtained is neutralized with a base and the aniline thus obtained is distilled.

As examples of products which may be employed in the process of the invention there may be mentioned 4-trichloromethylphenylisocyanate, 4-trichloromethylaniline carbamyl chloride, 4-tribromomethylphenylisocyanate, 4-tribromomethylaniline carbamyl bromide, 4-trichloromethyl-3-chloro phenylisocyanate, 4-trichloromethyl-3-nitrophenylisocyanate, 4-trichloromethyl-3,5-dichlorophenylisocyanate, 4-trichloromethyl-3-methylcarbonyl-phenylisocyanate and 4-trichloromethyl-3-isopropylphenylisocyanate.

The trifluoromethylanilines obtained by the process of the invention correspond to the general formula (II)

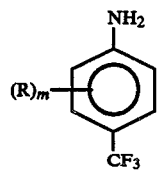

where R and m have the meanings given above for formula (I).

Among the anilines of the formula (II), para-trifluoromethyl-aniline may be mentioned especially.

The anilines obtained by the process of the present invention are used as synthesis intermediates in the pharmaceutical and plant protection industries and for the synthesis of dyes (U.S. Pat. No. 3,463,787 and French Pat. 1,520,220).

The present invention will be more easily understood with the aid of the examples which follow. The examples are given for illustration only and in no way limit the invention.

EXAMPLE 1

3-Chloro-4-amino-trifluoromethylbenzene

Into a 250 ml stainless steel reactor stirred with a magnetic bar and cooled to about 0° C. there are introduced successively, with stirring, 100 g (5 moles) of anhydrous HF, 3.6 g (0.2 mole) of water and 54.2 g (0.2 mole) of 2-chloro-4-trichloro-methylphenylisocyanate; the latter may be prepared by chlorination (with $Cl_2$) of 4-trichloromethylphenylisocyanate in situ. The reactor is closed and then heated to 50° C. for 3 hours 30 minutes. It is then cooled and the cooled reaction mixture is poured onto 200 g of crushed ice and then neutralized to pH 10 with a 50% strength potassium hydroxide solution, keeping the temperature below 20° C.

This aqueous phase is then extracted with 3 times 100 ml of methylene chloride. The organic phase are combined, dried and then evaporated under reduced pressure. About 31.5 g of a liquid compound essentially consisting of 3-chloro-4-amino-trifluoromethylbenzene (analyses by gas phase chromatography, infrared and mass spectrometry being carried out) are obtained.

EXAMPLE 2

4-Amino-trifluoromethylbenzene

A procedure identical to Example 1 is employed with the following compounds and conditions:

| | |
|---|---|
| hydrofluoric acid | 100 g (5 moles) |
| water | 1.8 g (0.1 mole) |
| 4-trichloromethyl-phenylisocyanate | 23.6 g (0.1 mole) |
| temperature | 60° C. |
| duration | 5 hours |

12.9 g of a liquid compound essentially consisting of p-trifluoromethylaniline are obtained.

EXAMPLE 3

Nitro-3-4-amino-trifluoromethylbenzene

A procedure identical to Example 1 is employed, with the following compounds and conditions:

| | |
|---|---|
| hydrofluoric acid | 100 g (5 moles) |
| water | 9 g (0.4 mole) |
| 2-nitro-4-trichloromethyl-phenyl-isocyanate | 125 g (0.4 mole) |
| temperature | 80° C. |
| duration | 6 hours |

56 g of a liquid compound essentially consisting of 3-nitro-4-amino-trifluoromethylbenzene are obtained.

I claim:

1. A process for the preparation of a para-trifluoromethylaniline which comprises the step of simultaneously performing, in liquid hydrofluoric acid in a closed reactor, hydrolysis with water and exchange fluorination of a para-trihalomethyl benzene isocyanate compound, wherein, of the three halogen atoms in the trihalomethyl radical, at least one is not fluorine, and wherein said compound may contain at least one substituent other than said isocyanate and said trihalomethyl group, said hydrolysis with water and exchange fluorination being conducted for a time sufficient to obtain said para-trifluoromethylaniline.

2. The process of claim 1, wherein said para-trihalomethylbenzene isocyanate has the formula (I):

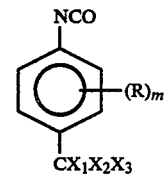

in which $X_1$, $X_2$ and $X_3$ are identical or different and each is a halogen atom, at least one of $X_1$, $X_2$ and $X_3$ not being fluorine, R is selected from the group consisting of halogen, $C_1$–$C_4$ alkyl, alkoxy, alkylthio, hydroxyl, carboxyl and nitro, and m is 0, 1 or 2.

3. The process of claim 2, wherein m is 1 or 2.

4. The process of claim 2, wherein m is 0.

5. The process of claim 1, wherein the reaction temperature is between 20° and 80° C.

6. The process of claim 1, wherein the reaction temperature is between 50° and 80° C.

7. The process of claim 4, wherein the compound of the formula (I) is para-trifluoromethylphenyl isocyanate.

8. The process of claim 2, wherein the hydrofluoric acid contains an amount of water such that the molar ratio of water to the compound of the formula (I) is between about 1 and 2.

9. The process of claim 8, wherein the hydrofluoric acid contains an amount of water such that the molar ratio of water to the compound of the formula (I) is about 1.

10. The process of claim 2, wherein the molar ratio of hydrofluoric acid to compound of the formula (I) is between about 5 and 50.

11. The process of claim 10, wherein the molar ratio of hydrofluoric acid to compound of the formula (I) is between about 12.5 and 50.

12. The process of claim 2, wherein the reaction temperature is between 20° and 80° C.

13. The process of claim 2, wherein the reaction temperature is between 50° and 80° C.

14. The process of claim 2, wherein R is selected from the group consisting of chlorine and nitro.

* * * * *

UNITED STATES PATENT AND TRADEMARK OFFICE
CERTIFICATE OF CORRECTION

PATENT NO. : 4,748,277

DATED : May 31, 1988

INVENTOR(S) : Michel Desbois

It is certified that error appears in the above-identified patent and that said Letters Patent is hereby corrected as shown below:

First page, Line 19 and 75, change the inventor's last name from "Debois" to --Desbois--.

Signed and Sealed this

Twenty-first Day of March, 1989

Attest:

Attesting Officer

DONALD J. QUIGG

Commissioner of Patents and Trademarks